United States Patent
Kurosaka et al.

(10) Patent No.: US 7,498,577 B2
(45) Date of Patent: Mar. 3, 2009

(54) SENSING DEVICE EMPLOYING ELECTROMAGNETIC WAVES

(75) Inventors: Ryoji Kurosaka, Kawasaki (JP); Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 69 days.

(21) Appl. No.: 11/717,714

(22) Filed: Mar. 14, 2007

(65) Prior Publication Data

US 2007/0215810 A1  Sep. 20, 2007

(30) Foreign Application Priority Data

Mar. 17, 2006  (JP) .............................. 2006-073612

(51) Int. Cl.
*G01S 13/00* (2006.01)
*G01J 1/00* (2006.01)

(52) U.S. Cl. .............................. 250/339.05; 250/341.1; 250/341.8; 250/336.1; 342/179

(58) Field of Classification Search ............ 250/339.05, 250/341.8
See application file for complete search history.

(56) References Cited

U.S. PATENT DOCUMENTS

| | | | |
|---|---|---|---|
| 5,623,145 | A | 4/1997 | Nuss |
| 5,710,430 | A | 1/1998 | Nuss |
| 6,448,553 | B1 | 9/2002 | Itsuji et al. |
| 6,835,925 | B2 | 12/2004 | Itsuji et al. |
| 7,248,995 | B2 | 7/2007 | Itsuji et al. |
| 2004/0202424 | A1* | 10/2004 | Cournoyer et al. ............ 385/39 |
| 2006/0061510 | A1 | 3/2006 | Itsuji |
| 2007/0017796 | A1* | 1/2007 | Hyde .................... 204/157.15 |
| 2007/0235718 | A1 | 10/2007 | Kasai et al. |

FOREIGN PATENT DOCUMENTS

JP  8-320254 A  12/1996

(Continued)

OTHER PUBLICATIONS

Cunningham, M.B., P.C. Padhya, C. Wood, L. Dazhang, M. Lachab, S.P. Khanna, E.H. Linfield, and A.G. Davies, "Evanescent-field Terahertz Time-domain Microscopy", Infrared and Millimeter Waves, 2007: 58-59.*

(Continued)

*Primary Examiner*—David P Porta
*Assistant Examiner*—Casey Bryant
(74) *Attorney, Agent, or Firm*—Fitzpatrick, Cella, Harper & Scinto

(57) ABSTRACT

A sensing device includes a transmission path, an electromagnetic-wave input unit through which an electromagnetic wave enters the transmission path, an electromagnetic-wave detector configured to detect the electromagnetic wave propagating through the transmission path, and a bent portion provided in the transmission path. The electromagnetic wave propagates through the transmission path while radiating to the periphery of the transmission path. The bent portion is provided in the transmission path for allowing an interaction to occur between a test subject and the electromagnetic wave in the transmission path. When the test subject is positioned relative to the bent portion, the electromagnetic-wave detector detects a change in the state of the electromagnetic wave caused by the interaction occurring between the test subject and the electromagnetic wave in the bent portion. The detected information provides a basis for obtaining information on the test subject.

8 Claims, 4 Drawing Sheets

FOREIGN PATENT DOCUMENTS

JP           2000-89042 A       3/2000

OTHER PUBLICATIONS

Mitrofanov, O., M. Lee, J.W.P. Hsu, I. Brener, R. Harel, J.F. Frederici, J.D. Wynn, L.N. Pfeiffer, and K.W. West, "Collection-Mode Near-Field Imaging with 0.5-THz Pulses", IEEE Journal on Selected Topics in Quantum Elec., vol. 7 (4): 600-7.*

"Millimeter Wave Proagation". Federal Communications Commission: Office of Engineering and Technology: Bulletin No. 70, Jul. 1997.*

Chaplin, Martin. "Water Absorption Spectrum". <http://www.lsbu.ac.uk/water/vibrat.html>: Nov. 20, 2008.*

Nature, vol. 432, p. 376, Nov. 18, 2004.

U.S. Appl. No. 11/785,771, filed Apr. 20, 2007.

U.S. Appl. No. 10/587,262, filed Mar. 22, 2006.

U.S. Appl. No. 11/751,517, filed May 21, 2007.

U.S. Appl. No. 11/802,113, filed May 21, 2007.

U.S. Appl. No. 11/843,423, filed Aug. 22, 2007.

* cited by examiner

SENSING DEVICE EMPLOYING ELECTROMAGNETIC WAVES

BACKGROUND OF THE INVENTION

1. Field of the Invention

The present invention relates to sensing devices that analyze physical properties of test subjects by means of electromagnetic waves in order to obtain information on the test subjects. In particular, the present invention relates to a sensing device that employs an electromagnetic wave (also referred to as a terahertz wave) within a frequency range of a millimeter-wave band to a terahertz band (30 GHz to 30 THz) in order to obtain information on a test subject.

2. Description of the Related Art

As devices for generating and detecting terahertz waves have been developed in recent years, technologies employing terahertz waves have been drawing much attention. For example, as an application field of terahertz waves, there have been researched and developed a technology for performing imaging using safe fluoroscopic devices to replace devices that employ X-rays, a spectroscopic technology for examining a complex dielectric constant or absorption spectrum of a material to check the bonding condition, a technology for analyzing biomolecules, and a communication technology.

Japanese Patent Laid-Open No. 8-320254 (corresponding to U.S. Pat. Nos. 5,710,430, 5,623,145) discloses a spectroscopic analysis device equipped with a spatial optical system that employs terahertz waves. Specifically, in this device, a terahertz wave is emitted towards a test subject, and a transmitted wave signal is measured by time-domain spectroscopy (THz-TDS). The signal is compared with a signal obtained when the test subject was not present (i.e. a reference signal) so as to determine the properties of the test subject from propagation delay and absorption spectrum. By scanning the terahertz wave or the test subject, a two-dimensional imaging operation can be performed.

Japanese Patent Laid-Open No. 2000-89042 discloses an optical fiber sensor that detects a leakage of a liquid. Specifically, an optical fiber is given a curved portion so that an electromagnetic wave exceeding a critical angle at the curved portion is forced to leak from a core layer. This electromagnetic wave and a test subject penetrated in a resin coating layer disposed on the exterior of a cladding layer are allowed to interact with each other, whereby the test subject can be detected. Furthermore, Nature, Vol. 432, p. 376, 2004 discloses a technology for allowing a terahertz wave to propagate through a single line, and discusses the low-loss and low-dispersion properties of a single line within the terahertz-wave band.

However, with regard to Japanese Patent Laid-Open No. 8-320254, since the device uses a spatial optical system for the analysis of the test subject, the analysis may be easily affected by moisture in the air. This is because an energy band that corresponds to modes such as vibration and rotation of water molecules in the moisture vapor is present within the terahertz-wave band, causing the terahertz wave to be absorbed by the water molecules. Therefore, in a spatial optical system that employs terahertz waves, the propagation of a terahertz wave is usually performed within a nitrogen atmosphere or in vacuum. However, since the terahertz waves have properties in which they are easily susceptible to moisture in the air, an analysis technique that can reduce the effect of moisture in the air and increase the electromagnetic-wave propagation density to allow the electromagnetic waves to extend over a wider band is in demand.

On the other hand, Japanese Patent Laid-Open No. 2000-89042 is merely a disclosure of a technology that employs the transmissibility of light through an optical fiber constituted by a core layer and a cladding layer. Likewise, Nature, Vol. 432, p. 376, 2004 is merely a disclosure of a wire transmission path formed of a single conductor.

SUMMARY OF THE INVENTION

The present invention provides a sensing device that includes a transmission path, an electromagnetic-wave input unit through which an electromagnetic wave enters the transmission path, an electromagnetic-wave detector configured to detect the electromagnetic wave propagating through the transmission path, and a bent portion provided in the transmission path. The electromagnetic wave propagates through the transmission path while radiating to the periphery of the transmission path. The bent portion is provided in the transmission path for allowing an interaction to occur between a test subject and the electromagnetic wave in the transmission path. When the test subject is positioned near the bent portion, the electromagnetic-wave detector detects a change in the state of the electromagnetic wave, such as the properties thereof, caused by the interaction occurring between the test subject and the electromagnetic wave in the bent portion. The detected state provides a basis for obtaining information on the test subject.

Furthermore, the present invention provides an imaging apparatus that includes the aforementioned sensing device additionally provided with a scanning unit configured to scan areas of interaction between the test subject and the bent portion occurring at the bent portion, and a circuit system that performs imaging of the test subject. When the test subject is positioned near the bent portion, the scanning unit scans the interaction areas while the electromagnetic-wave detector detects a change in the state of the electromagnetic wave caused by the interaction between the test subject and the electromagnetic wave occurring at the bent portion. The circuit system obtains information on the test subject in each interaction area on the basis of the detected state. The imaging of the test subject is performed on the basis of the obtained information.

According to the present invention, the transmission path has the bent portion, and the electromagnetic wave propagates through the transmission path while radiating to the periphery of the transmission path. Thus, with relatively low loss, the electromagnetic wave can be transmitted to the bent portion where the test subject and the electromagnetic wave interact with each other. In other words, in comparison to a spatial optical system, an effect of interaction with moisture in the air can be reduced. Furthermore, since the transmission path has a bent structure, an area where the test subject and the electromagnetic wave interact with each other in the transmission path can be restricted to the bent portion. Moreover, for the test subject, the interaction area with respect to the electromagnetic wave can similarly be restricted to an area near the bent portion, whereby the spatial resolution in the process for obtaining the test-subject information, such as the analysis and imaging processes of the test subject, can be increased.

Further features of the present invention will become apparent from the following description of exemplary embodiments with reference to the attached drawings.

DESCRIPTION OF EMBODIMENTS

First Exemplary Embodiment

Figure 1:
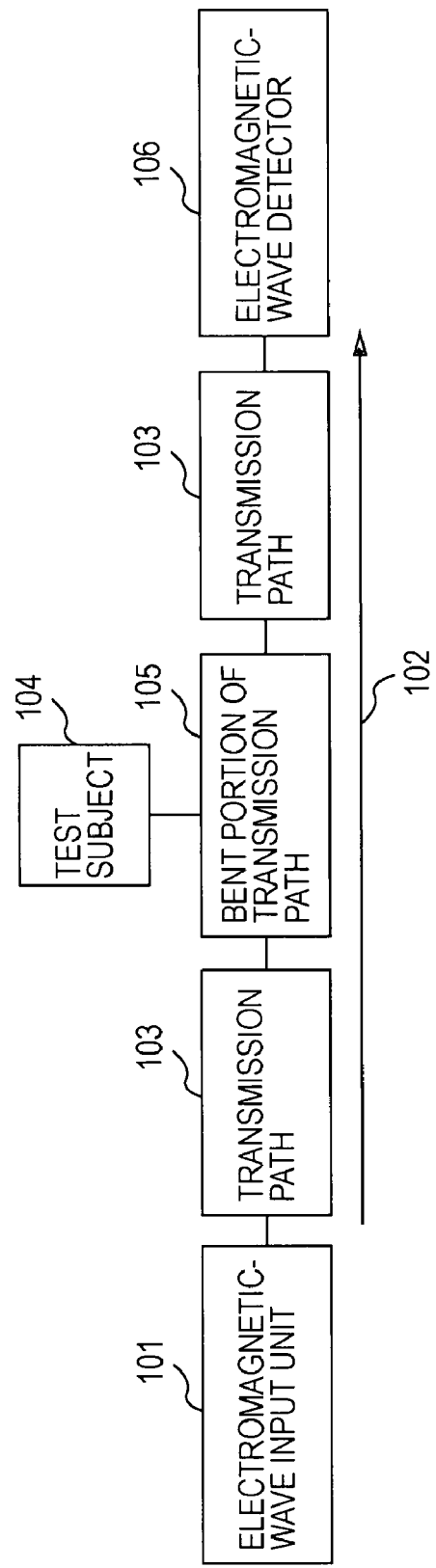
FIG. 1 is a block diagram of a sensing device according to a first exemplary embodiment of the present invention.

A first exemplary embodiment of the present invention will now be described. An embodiment shown in FIG. 1 includes an electromagnetic-wave input unit 101, a transmission path 103, a bent portion 105 provided in the transmission path 103 for increasing an interaction effect between a test subject 104 and an electromagnetic wave 102, and an electromagnetic-wave detector 106. The electromagnetic wave 102 propagates through the transmission path 103 while radiating to the periphery of the transmission path 103. The transmission path 103 can transmit the electromagnetic wave 102 with high electromagnetic-wave density and good controllability in a specific direction. For example, with regard to terahertz waves, a single line serving as the transmission path 103 can transmit the electromagnetic wave 102 with low loss and low dispersion (see Nature, Vol. 432, p. 376, 2004). In addition to being a section where the electromagnetic wave 102 propagating through the transmission path 103 and the test subject 104, which is a subject to be measured, interact with each other, the bent portion 105 is also a section that allows the electromagnetic wave 102 to interact with only a small designated area of the test subject 104.

The electromagnetic-wave input unit 101 may be formed by, for example, employing a cross-wire structure (see FIGS. 3, 4A and 4B) or by giving the transmission path 103 a grating structure. In another embodiment, the electromagnetic-wave input unit 101 may be formed by attaching a photoconductor element equipped with a compound semiconductor of, for example, GaAs to an end surface of the transmission path 103 or by giving the transmission path 103 an antenna structure. However, the technique for forming the electromagnetic-wave input unit 101 is not limited to those mentioned above. Any type of technique is permissible as long as the electromagnetic-wave input unit 101 provides a high coupling efficiency between the transmission path 103 and the electromagnetic wave 102 generated inside or outside of the transmission path 103.

The electromagnetic-wave detector 106 may be formed by, for example, attaching a photoconductor element onto an end surface of the transmission path 103 or by using an electro-optic crystal. However, the technique for forming the electromagnetic-wave detector 106 is not limited to those mentioned above. Any type of technique is permissible as long as the electromagnetic wave 102 transmitted through the transmission path 103 can be accurately detected.

A detection principle of an analysis of the interaction effect between an electromagnetic wave propagating through a transmission path and a test subject will be described below with reference to FIG. 2. A transmission path 201 has various electromagnetic-field modes for the electromagnetic wave being transmitted. For example, in a transmission path such as a single line, a coplanar strip line, and a micro strip line, there are electromagnetic waves that propagate through the transmission path 201 while radiating into the surrounding space. There are also electromagnetic waves that are radiated from the transmission path 201. Furthermore, there is also a near-field which is a neighboring field generated only near the transmission path 201.

Figure 2:
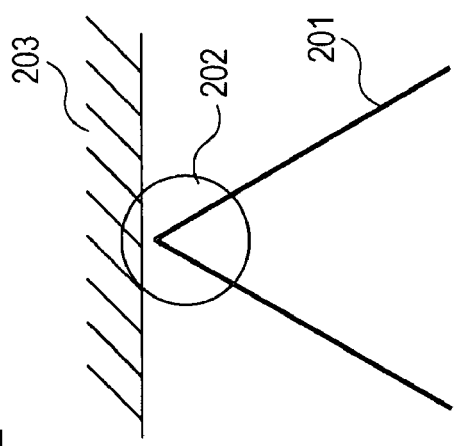
FIG. 2 illustrates a detection principle of a sensing device according to an exemplary embodiment of the present invention.

In this embodiment, reference numeral 202 in FIG. 2 denotes both the electromagnetic wave propagating through the transmission path 201 while radiating into the surrounding space and the near-field generated only near the transmission path 201. By allowing this electromagnetic wave and the near-field to interact with a test subject 203, the test subject 203 can be analyzed. This analysis employs an electromagnetic-field mode that is created as a result of the bending of the transmission path 201. When the transmission path 201 is bent and the distance between the bent portion and the test subject 203 becomes approximately equal to or less than the wavelength of the electromagnetic wave, the interaction between the test subject 203 and the electromagnetic wave becomes prominent. Moreover, by giving the transmission path 201 a bent structure, the area of the test subject 203 that interacts with the electromagnetic wave propagating through the transmission path 201 can be limited to a small area. The interaction effect between the test subject 203 and the electromagnetic wave can be detected by means of a segment of the transmission path 201 at the downstream side of the bent portion and also by the electromagnetic-wave detector. In one advantage of this case, since the transmission path 201 is not cut off at the bent portion, it is unnecessary to adopt a unit for recoupling the electromagnetic wave to the segment of the transmission path 201 at the downstream side of the bent portion.

Second Exemplary Embodiment

A sensing device according to a second exemplary embodiment of the present invention will be described below with reference to FIG. 3. The sensing device of the second embodiment includes an electromagnetic-wave input unit 301, a transmission path 303, a bent portion 305 provided in the transmission path 303 for increasing an interaction effect between a test subject 304 and an electromagnetic wave 302, an electromagnetic-wave detector 306, and a transmission-path scanning unit 307.

The transmission path 303 is defined by a single line so that the electromagnetic wave 302 can be transmitted with low loss and low dispersion. The transmission path 303 does not necessarily need to be defined by a single line and may be of any type of line that allows for low-loss and low-dispersion transmissibility. For example, the transmission path 303 may be defined by a coplanar strip line or may have a photonic crystal structure formed by giving a periodic structure to a coating layer wrapped around a wire. In the case where a coplanar strip line is used, the following configurations, for example, are possible. In one configuration, a coplanar strip line having a bent portion (which is to become the bent portion 305 of the transmission path 303) is disposed on a substrate. In another configuration, a coplanar strip line is formed on a substrate of a high bending strength material and the substrate is bent so that the transmission path is given a bent structure. The line is preferably composed of a material having low electrical resistance and low loss. For example, as a metal wire such as a copper wire, a metal line having a bending pattern may be deposited on a silicon wafer so as to form a single line. This helps prevent the electromagnetic wave from being lost by Joule heat when the electromagnetic wave passes through a medium that has limited resistance.

The distance between the bent portion 305 of the transmission path 303 and the test subject 304 is preferably set equal to or less than a value at which a near-field (neighboring field) generated by the electromagnetic wave 302 propagating through the transmission path 303 is prominent. In detail, a distance at which a neighboring field occurs is approximately equal to or less than the wavelength of the electromagnetic wave 302 propagating through the transmission path 303. If an electromagnetic wave has a wavelength of 1 THz, the distance is about 100 μm. Consequently, the distance between the bent portion 305 and the test subject 304 opposed to the bent portion 305 is preferably set such that the bent portion 305 and an area of the test subject 304 that is closest to the bent portion 305 have a distance therebetween that is substantially equal to or less than the wavelength of the electromagnetic wave 302.

Figure 4A:
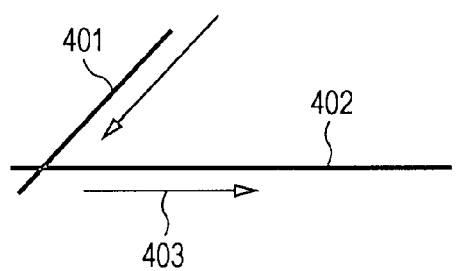
FIG. 4 illustrates a cross-wire structure.
Figure 4B:
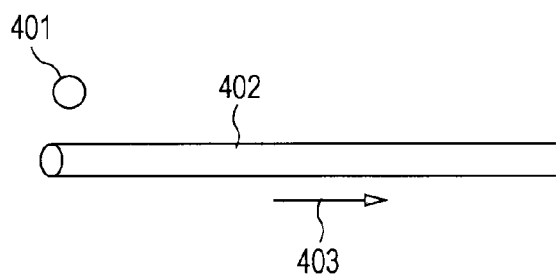

In the second embodiment, the electromagnetic-wave input unit 301 through which a terahertz wave can enter the transmission path 303 is specifically an input unit that employs a cross-wire structure. FIGS. 4A and 4B show an illustrative example of a cross-wire structure. FIG. 4A is a perspective view and FIG. 4B is a diagram that is viewed in a direction in which a first wire 401 extends. The first wire 401 and a second wire 402 are disposed perpendicular to each other so that an electromagnetic wave 403 can be transmitted from the first wire 401 to the second wire 402.

Meanwhile, the transmission-path scanning unit 307 changes the interaction area of the bent portion 305, at which the electromagnetic wave 302 propagating through the transmission path 303 and the test subject 304 interact with each other, in a scanning fashion so as to perform an imaging operation of the test subject 304. In one embodiment, this scanning unit may be achieved by securing the transmission path 303 to a movable stage. In another embodiment, a scanning unit configured to move the test subject 304 for scanning is also permissible.

As another type of a scanning unit, a plurality of transmission paths of the same kind may be arranged near the surface of the test subject 304, such that the scanning unit may scan measurement sections of the test subject 304 by continuously switching electromagnetic-wave detectors detecting the electromagnetic wave 302 interacting with the test subject 304 one after another. In that case, the distance among the bent portions of the plurality of transmission paths is preferably set equal to or greater than the wavelength of the electromagnetic wave in order to reduce the effect of interactions between the test subject 304 and the electromagnetic wave 302 among the measurement sections. In another type of scanning unit, the transmission path 303 may be moved by, for example, raster scanning (see arrows on the surface of the test subject 304 in FIG. 3) in order to analyze the entire surface of the test subject 304.

The electromagnetic-wave detector 306 may be defined by a photoconductor element equipped with a femtosecond laser formed by attaching a compound semiconductor of, for example, GaAs onto an end surface of a single line. This allows for detection of current modulation occurring at the photoconductor element in response to the electromagnetic wave interacting with the test subject 304. Other types of electromagnetic-wave detectors are also permissible. In another type of an electromagnetic-wave detector, the electromagnetic wave propagating through the transmission path 303 is first transmitted from the transmission path 303 to a cross-wire structure before it is detected by the photoconductor element attached to an end of the cross-wire structure. In the latter type, it is not necessary to move the end of the cross-wire structure that crosses the transmission path 303, and therefore, the latter type is suitable for detecting using a photoconductor element equipped with a femtosecond laser and the like.

The magnitude of a peak value of a signal waveform (such as a current waveform) obtained as a result of the above is converted to an appropriate gray-scale level by a circuit system. The test subject can be imaged on the basis of a change in the gray-scale level. Accordingly, the interaction areas between the electromagnetic wave 302 propagating through the transmission path 303 and the test subject 304 can be scanned by the transmission-path scanning unit 307, whereby the entire surface of the test subject 304 can be analyzed. The test subject 304 is preferably biomolecules, which are sensitive to the terahertz band. By providing the scanning unit and the circuit system that performs the imaging, the surface information of each scanned area of the test subject interacting with the electromagnetic wave at the bent portion can be extracted by the circuit system on the basis of the information of the detected electromagnetic wave, whereby the imaging of the test subject can be implemented.

Third Exemplary Embodiment

Figure 5:
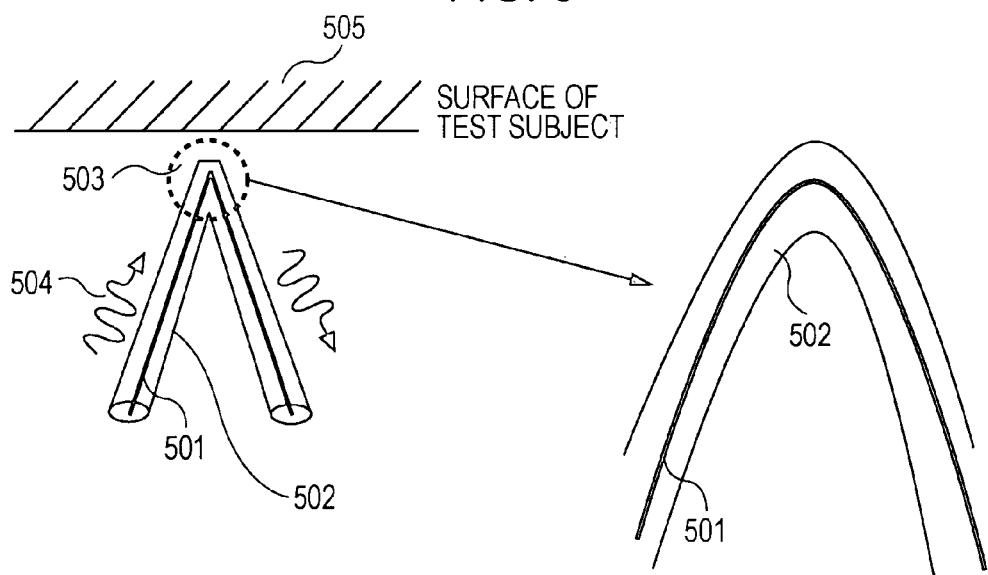
FIG. 5 illustrates a sensing device according to a third exemplary embodiment of the present invention.

FIG. 5 illustrates a third exemplary embodiment of the present invention. A sensing device according to the third embodiment includes an electromagnetic-wave input unit, an electromagnetic-wave detector, a transmission path, a bent portion, and a transmission-path coating structure. In FIG. 5, a transmission path 501, a transmission-path coating structure 502, a bent portion 503, an electromagnetic wave 504, and a test subject 505 are illustrated. The transmission path 501 is coated with the transmission-path coating structure 502. The transmission-path coating structure 502 is provided for reducing an interaction effect between the electromagnetic wave 504 and the atmosphere at sections of the transmission path 501 excluding the bent portion 503. This reduces fluctuation in the electromagnetic wave caused by moisture in the air, thereby increasing the signal-to-noise ratio. The transmission-path coating structure 502 for covering the transmission path 501 is preferably composed of a dielectric material, which has low dispersibility.

Figure 3:
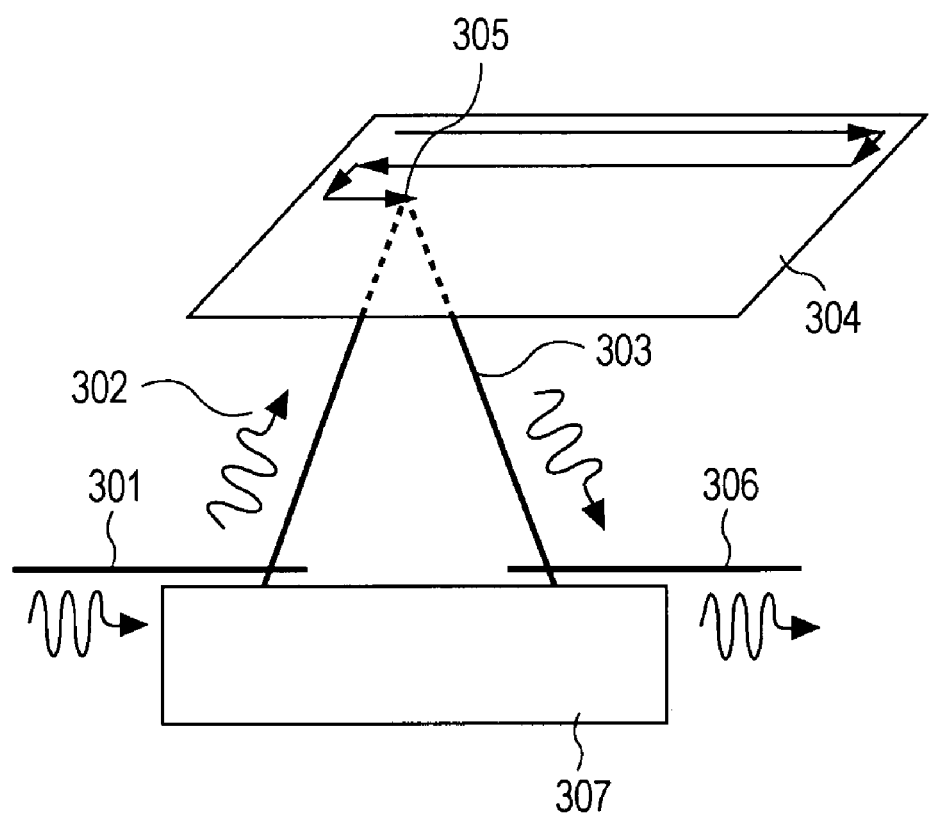
FIG. 3 illustrates a sensing device according to a second exemplary embodiment of the present invention.

In the third embodiment, the transmission path 501 is defined by a single line, and the electromagnetic-wave input unit and the electromagnetic-wave detector are given a cross-wire structure, such as the one shown in FIGS. 3, 4A and 4B. The transmission-path coating structure 502 is formed by attaching an electromagnetic-wave coating of a dielectric material around a periphery of a metal wire serving as a single line. For example, the metal wire may be attached to the center of a columnar mold, and a resin material which is to become the transmission-path coating structure may be cast into the mold, and the dielectric material may be burned until it is hardened. The metal wire 501 coated with the transmission-path coating structure 502 may then be bent together with the transmission-path coating structure 502 so that the bent portion 503 can be formed. Furthermore, for example, the transmission-path coating structure 502 may be partly scraped, and the scraped section may then be changed in shape, or the transmission-path coating structure 502 may be partly scraped so that the transmission path 501 can be exposed through the scraped section of the transmission-path coating structure 502 at the bent portion 503. This allows the test subject 505 and the electromagnetic wave 504 to be closer to each other. The other features are the same as those in the second embodiment.

Fourth Exemplary Embodiment

Figure 6:
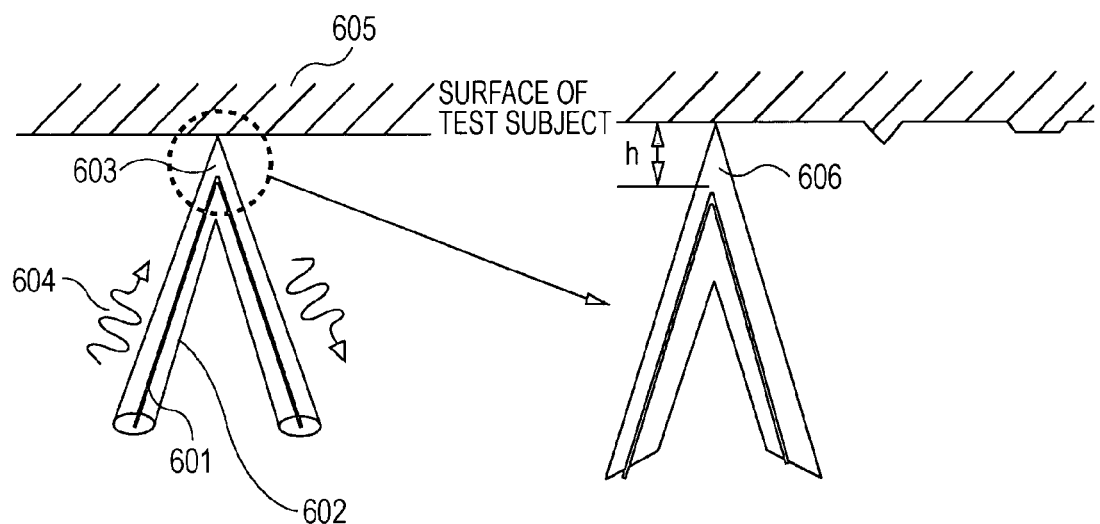
FIG. 6 illustrates a sensing device according to a fourth exemplary embodiment of the present invention.

FIG. 6 illustrates a fourth exemplary embodiment of the present invention. A sensing device according to the fourth embodiment includes an electromagnetic-wave input unit, an electromagnetic-wave detector, a transmission path, a bent portion, a transmission-path coating structure, and a spacer. In FIG. 6, a transmission path 601, a transmission-path coating structure 602, a bent portion 603, an electromagnetic wave 604, a test subject 605, and a spacer 606 are illustrated.

In the spacer 606, the magnitude of the electromagnetic wave 604 changes with increasing distance from the transmission path 601. Therefore, the spacer 606 is provided for maintaining a fixed distance between the transmission path 601 and the measurement area (i.e. the surface) of the test subject 605 at the bent portion 603. The spacer 606 is formed by processing the transmission-path coating structure 602 that covers the transmission path 601. As shown in FIG. 6, the spacer 606 is defined by a protrusion formed at the tip end of the bent portion 603.

In detail, the spacer 606 is formed by, for example, applying a dielectric material, by spin coating, onto a wafer having a metal wire bonded thereto or a wafer having a transmission path patterned thereon by deposition. Subsequently, the wafer undergoes a photolithography step, an etching step, and a resist-removing step, thereby forming the spacer 606. The end portion of the spacer 606 preferably has a protruding structure. Such a structure allows for a less contact area between the surface of the test subject 605 and the transmission-path coating structure 602. This improves the position resolution so as to properly correspond to irregularities on the surface of the test subject 605 (see the enlarged right section of FIG. 6), whereby an accurate analysis can be achieved. As mentioned above, a distance (h) between the transmission path 601 and the surface of the test subject 605 at the bent portion 603 is preferably equal to or less than the order of wavelength of the electromagnetic wave 604 at which an interaction effect caused by a near-field is prominent. The other features are the same as those in the above embodiments.

Fifth Exemplary Embodiment

Figure 7:
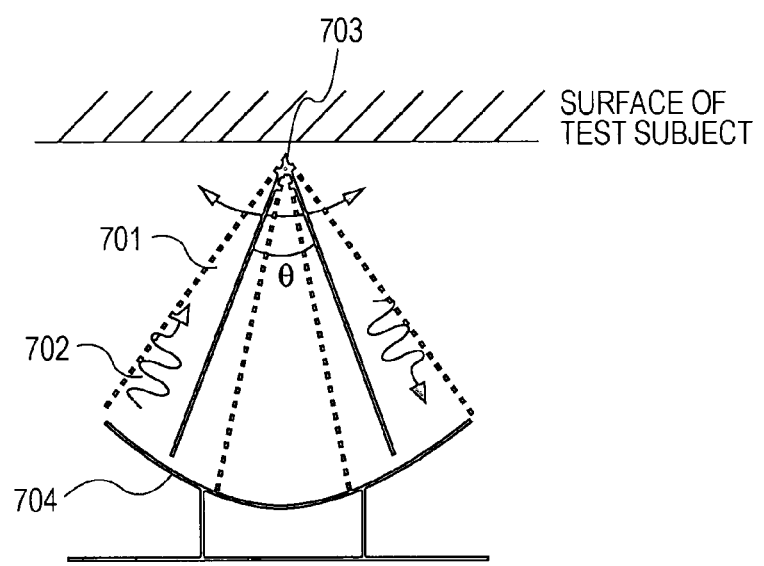
FIG. 7 illustrates a sensing device according to a fifth exemplary embodiment of the present invention.

FIG. 7 illustrates a fifth exemplary embodiment of the present invention. A sensing device according to the fifth embodiment includes an electromagnetic-wave input unit, a transmission path, a bent portion provided in the transmission path for increasing an interaction effect between a test subject and an electromagnetic wave, a mechanism configured to temporally modulate the bent angle of the bent portion, and an electromagnetic-wave detector. In FIG. 7, a transmission path 701, an electromagnetic wave 702, a bent portion 703, and a driving element 704 serving as an angle modulation unit that adjusts the bent angle of the bent portion 703 are illustrated.

In the fifth embodiment, the driving element 704 is used to periodically change an angle θ of the bent portion 703 so as to temporally modulate the electric-field distribution at the bent portion 703. Consequently, by using a lock-in amplifier or the like to perform demodulation, a highly sensitive synchronous detection can be achieved. In addition, by modulating the bent angle, the electric-field distribution in the vicinity of the transmission path 701 can be changed, whereby the distance of interaction between the test subject and an electromagnetic-field mode constituted by the electromagnetic wave 702 and the near-field can be changed. Furthermore, by modulating the bent angle, the occurrence of interaction between the test subject and the electromagnetic-field mode can be changed depending on the frequency band, thereby allowing for wavelength selectivity.

The ends of the transmission path 701 may be fixed to the driving element 704, which is movable along a rail. Thus, the bent angle of the bent portion 703 can be controlled by moving the driving element 704 on the rail. In that case, the rail is given a circular arc shape as shown in FIG. 7 so that a fixed distance can be maintained between the bent portion 703 and the surface of the test subject. In addition, a sensor that is capable of detecting the bent angle may be attached to the driving element 704 to achieve higher controllability. The bent angle can be calculated from position information that indicates where in the rail the driving element 704 is positioned. The driving element 704 serving as an angle modulation unit in the fourth embodiment may be applied to each of the above-described embodiments. The other features are the same as those in the above embodiments.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-073612 filed Mar. 17, 2006, which is hereby incorporated by reference herein in its entirety.

What is claimed is:

1. A sensing device comprising:
   a transmission path through which an electromagnetic wave propagates while radiating to the periphery of the transmission path, wherein the transmission path includes a line made of a conductive material and the frequency of the electromagnetic wave is within a range of 30 GHz to 30 THz;
   an electromagnetic-wave input unit through which the electromagnetic wave enters the transmission path;
   an electromagnetic-wave detector configured to detect the electromagnetic wave propagating through the transmission path; and
   a bent portion provided in the transmission path for allowing an interaction to occur between a test subject and the electromagnetic wave in the transmission path,
   wherein when the test subject is positioned near the bent portion, the electromagnetic-wave detector detects a change in a state of the electromagnetic wave caused by the interaction occurring between the test subject and the electromagnetic wave in the bent portion, the detected change providing a basis for obtaining information on the test subject.

2. The sensing device according to claim 1, wherein a distance between the bent portion of the transmission path and an area of the test subject that is closest to the bent portion is set substantially equal to or less than the wavelength of the electromagnetic wave.

3. The sensing device according to claim 1, wherein the transmission path is given a coating.

4. The sensing device according to claim 1, wherein the bent portion is provided with a spacer that sets the distance between the bent portion of the transmission path and the test subject.

5. The sensing device according to claim 1, further comprising an angle modulation unit configured to modulate a bent angle of the bent portion.

6. The sensing device according to claim 1, wherein the transmission path comprises a single line.

7. The sensing device according to claim 1, further comprising a scanning unit configured to scan areas of interaction between the test subject and the bent portion occurring at the bent portion.

8. An imaging apparatus comprising:

the sensing device according to claim 7; and a circuit system that performs imaging of the test subject, wherein when the test subject is positioned near the bent portion, the scanning unit scans the interaction areas while the electromagnetic-wave detector detects a change in the state of the electromagnetic wave caused by the interaction between the test subject and the electromagnetic wave occurring at the bent portion, wherein the circuit system obtains information on the test subject in each interaction area on the basis of the detected change, and wherein the imaging of the test subject is performed on the basis of the obtained information.

* * * * *